United States Patent
Larsson

Patent Number: 6,039,717
Date of Patent: Mar. 21, 2000

[54] ADHESIVE FASTENING DEVICE

[75] Inventor: Björn Larsson, Örsviksvägen, Sweden

[73] Assignee: SCA Hygiene Products AB, Goteborg, Sweden

[21] Appl. No.: 09/000,248
[22] PCT Filed: Jul. 12, 1996
[86] PCT No.: PCT/SE96/00946
   § 371 Date: Jan. 23, 1998
   § 102(e) Date: Feb. 2, 1998
[87] PCT Pub. No.: WO97/05842
   PCT Pub. Date: Feb. 20, 1997

[30] Foreign Application Priority Data

Aug. 3, 1995 [SE] Sweden ................. 9502747

[51] Int. Cl.$^7$ ..................... A61F 13/15
[52] U.S. Cl. ............ 604/391; 604/358; 604/365; 604/385.1; 604/386; 604/387; 604/389
[58] Field of Search ................. 428/41.7, 41.8, 428/354, 355, 355 RA; 604/385.1, 385.2, 385, 389, 358, 365, 386, 387, 391

[56] References Cited

U.S. PATENT DOCUMENTS

| 4,010,753 | 3/1977 | Tritsch . |
| 4,067,337 | 1/1978 | Ness . |
| 4,336,804 | 6/1982 | Roeder . |
| 4,337,772 | 7/1982 | Roeder . |
| 4,376,440 | 3/1983 | Whitehead et al. . |

FOREIGN PATENT DOCUMENTS

| 0 229 639 A2 | 1/1987 | European Pat. Off. . |
| 0 234 194 A2 | 9/1987 | European Pat. Off. . |
| 0 393 953 A2 | 10/1990 | European Pat. Off. . |
| 0 471 384 A1 | 2/1992 | European Pat. Off. . |
| 0 471 385 A1 | 2/1992 | European Pat. Off. . |
| 0 471 386 A2 | 2/1992 | European Pat. Off. . |
| 0 471 387 A2 | 2/1992 | European Pat. Off. . |
| 2 366 009 | 4/1978 | France . |

Primary Examiner—John G. Weiss
Assistant Examiner—Miley Craig Peppers
Attorney, Agent, or Firm—Burns, Doane, Swecker & Mathis, L.L.P.

[57] ABSTRACT

The invention relates to a fastening device (1) for releaseable fastening onto textile or textile-like material surfaces, comprising a self-adhesive, pressure sensitive layer (2) with a first surface intended to be firmly fixed against a substrate, as well as a second surface intended to serve as a fastening surface onto the textile or textile-like material surface. What primarily distinguishes the invention is that an essentially incompressible, non-adhesive covering layer (3), with a thickness which does not exceed 0.5 mm and which has a plurality of penetrating openings or pores (4) arranged essentially perpendicularly to the plane of the covering layer (3), is arranged on and fastened to the fastening surface of the adhesive layer (2), wherein the relative distance between two adjacent openings or pores (4) in the covering layer (3) does not exceed 3 mm, whereby the fastening means is suitable for co-operating with a textile or textile-like receiving surface (5).

The invention also includes absorbent products such as diapers, sanitary napkins, panty-liners, incontinence pads, bed protectors, seat protectors or the like, comprising such a fastening means.

8 Claims, 2 Drawing Sheets

ADHESIVE FASTENING DEVICE

TECHNICAL FIELD

The present invention relates to a fastening device for fastening onto textile or textile-like material surfaces, comprising a self-adhesive, pressure sensitive layer with a first surface intended to be firmly joined to a substrate, and a second surface intended to serve as a surface which fastens onto the textile or textile-like material surface.

The invention also concerns an absorbent article such as a sanitary napkin, an incontinence guard, a seat cover or a bed protector comprising such a fastening device.

A diaper in accordance with the invention comprises a first liquid-permeable casing layer, a second liquid impermeable casing layer, which layers are mutually joined around an absorption body enclosed between the casing layers, and which has a front part, a rear part, and a narrow crotch part arranged between these two parts, and two longitudinal side edges, a front waist edge and a rear waist edge, which are shaped to together encircle the user's waist and thereby form the diaper's waist opening. The diaper further comprises fastening tabs, which are arranged on the longitudinal side edges, near the rear waist edge, and are intended to fasten onto the front part for fastening the diaper together to a pants-like shape.

BACKGROUND OF THE INVENTION

The most common way to fasten a sanitary napkin inside a pair of underpants during use has up to now been to arrange a fastening surface in the form of pressure-sensitive adhesive on the side of the napkin which during use is intended to be in contact with the underpants of the user. In order to avoid adhesion problems with the adhesive surface during storage and transport of the napkins, the fastening adhesive is usually protected with a special removeable strip of material made of release agent treated paper, or similar. When the napkin is to be used, the protective strip is removed, so that the adhesive is exposed and can be used for fastening of the napkin in the underpants of the user. The protective strip does not have any further function, but is thrown away after it has been released from the fastening adhesive. The use of such protective strips has a number of disadvantages. For example, it is awkward to handle the protective strips when the sanitary napkin is to be used, especially if the sanitary napkin is provided with several different protective strips which have to be removed. Furthermore, the use of protective strips results in the use of unnecessarily large amounts of material, which is a disadvantage from an environmental and energy point of view, as well as with respect to costs.

In order to eliminate the special protective strips, it is known to provide a sanitary napkin with adhesive regions as well as release agent treated regions arranged in such a way that the sanitary napkin can be folded together with the adhesive regions in contact with and protected by the release agent treated regions. Such sanitary napkins are described in U.S. Pat. No. 4,376,440, EP 471,384, EP 471,385, EP 471,386 and EP 471,387.

Such an arrangement brings about a reduction in material consumption as well as certain simplifications in handling the sanitary napkin. A principal problem and a big disadvantage with it is, however, that the possibility of applying the fastening adhesive in the way which gives the best anchoring of the sanitary napkin inside the user's underpants, is greatly limited, since the placing of the adhesive surface primarily must be chosen so that the adhesive surface after folding together of the sanitary napkin lies in contact with the corresponding release agent treated area.

From EP 393,953 a pressure sensitive adhesive fastening device is known, which comprises a carrier of which one side is equipped with a pressure sensitive adhesive, arranged in the spaces between a series of pegs or projections, projecting out from the carrier, wherein the pegs or projections extend out beyond the adhesive. The fastening device is especially suitable for use on cloth, whereby the pegs or projections are able to penetrate the surface of the cloth so that the adhesive is brought into contact with, and adheres to, the cloth. The problems with such a known fastening means are that they are relatively expensive and complicated to manufacture, and further that they are stiff and hard and for this reason easily cause chafing or other discomfort to the user. Furthermore, the projecting tabs involve a certain risk of damage to the surface which the arrangement is fastened to. A similar adhesive fastening device is described in U.S. Pat. No. 4,376,440.

U.S. Pat. No. 4,336,804 and U.S. Pat. No. 4,337,772 describe sanitary napkins with fastening devices made of a combination of parts with sticky adhesive and parts with non-sticky adhesive. The non-sticky adhesive is thereby arranged so that its surface which is facing away from the sanitary napkin is located at a greater distance from the napkin than the corresponding surface on the sticky adhesive. Such an arrangement of adhesive is, however, comparatively complicated to manufacture, as it requires two adhesive applicators which must be synchronized. This naturally also means that the manufacturing of the known sanitary napkins becomes unnecessarily expensive.

A further sanitary napkin with an adhesive fastening device is described in EP 234,194 and EP 229,639. This known sanitary napkin comprises a pressure sensitive fastening adhesive layer, as well as an elastic foam material layer applied on the outside of the adhesive layer and provided with openings through which the adhesive is exposed for fastening. Such a fastening device has not a sufficiently large available fastening area so as to be able to achieve a satisfactory fastening. Furthermore, there are difficulties during manufacture of the a known sanitary napkin, as a web of foam material is relatively fragile and easily breaks when it is subjected to the tensile forces which occur during high production speeds. Furthermore, at high production speeds, it is hard to control and regulate the stretching which occurs in the elastic foam material. Furthermore, the foam material is expensive and difficult to manufacture in the form of a sufficiently thin layer to enable the adhesive to be effective through the foam layer. Furthermore, a thick bulky material is difficult to handle in a continuous process, as it requires frequent roll changes, which naturally negatively influence the effectivity and cost.

A further problem with the earlier known sanitary napkins with a fastening means in the form of a coating of pressure sensitive adhesive, is that it is difficult to control the degree of adhesion, so that it is sufficiently great, irrespective of which type of material the underpants of the user are made of. The adhesive capacity is of different strength for different textile materials and one and the same adhesive coating can fasten many times better on a surface of nylon, or nylon-type material than on a material of cotton. In the case of an adhesive coating which gives sufficiently good fastening in underpants made of cotton, there is the risk that a pair of underpants made of nylon or similar are damaged when the napkin is removed, or that traces of adhesive remain in the underpants.

Diapers of the type described in the introduction have up to now been fastened together by means of tape tabs which are fastened against a reinforced plastic surface on the front part of the diaper. Even if such a fastening system offers a satisfactory fastening of the diaper, it is still, however, connected with certain disadvantages. For example, it is complicated to protect the tape tabs before use. This is solved on the known diapers by folding the tabs in towards release agent treated surfaces either on the tabs themselves, or on the diaper. Folded tabs are expensive and complicated to manufacture and apply to the diapers and are the cause of a relatively large amount of the waste which occurs when the diapers are manufactured. Furthermore, it can be hard to pick the tape free from the release agent treated surface when the diaper is to be used. Especially when applying the diaper to a very lively child, difficulty in opening the tabs can be irritating. In order to increase the ease of handling of the tape tabs, these are manufactured from fairly stiff material which can easily produce sharp corners and edges which may cause chafing and irritation to the user's skin.

OBJECT OF THE INVENTION

The object of the present invention is to produce an improved fastening device for fastening onto textile or textile-like material, which provides a way of avoiding the problems with the earlier known fastening arrangements.

SHORT DESCRIPTION OF THE INVENTION

A fastening device made according to the invention and comprising a pressure-sensitive adhesive layer, is primarily characterized in that an essentially incompressible, non-adhesive covering layer, with a thickness which does not exceed 0.5 mm and having a plurality of penetrating openings or pores arranged essentially perpendicularly to the plane of the covering layer, is arranged on top of and fastened to the fastening surface of the adhesive layer, wherein the distance between two adjacent openings or pores in the covering layer is not greater than 3 mm, whereby the fastening means is intended to cooperate with a textile or textile-like receiving surface, but displays low or no adhesive capability onto smooth materials with low drapability, or onto itself.

The covering layer according to one embodiment of the invention is a plastic net, or a perforated plastic film. According to another embodiment, the covering layer is made of a layer of a non-woven web, known as non-woven, or of a loose weave.

An absorbent product made according to the invention comprises an absorption body enclosed in a casing and further comprises fastening means comprising a pressure sensitive adhesive layer. The product is distinguished principally by an essentially incompressible, non-adhesive covering layer with a thickness which is not greater than 0.5 mm and having a plurality of penetrating openings or pores, which layer is arranged on and fastened to the adhesive layer surface which faces away from the product, wherein the distance between two adjacent openings or pores in the covering layer is not greater than 3 mm, whereby the fastening means is fastenable against porous textile or textile-like material surfaces, but has low or no adhesive capacity on smooth materials with low drapability, or on itself.

A diaper according to the invention is characterized principally in that it comprises fastening means formed from a self-adhesive layer covered by an essentially incompressible, non-adhesive covering layer which has a plurality of penetrating openings or pores. During use, the diaper is fastened together at the sides, so that it, in the same manner as a pair of pants, surrounds the lower part of the trunk of the user. The fastening together takes place by means of fastening tabs arranged on the rear part of the diaper being fastened to the front part of the diaper. The fastening device can either be arranged on the fastening tabs or on the front part of the diaper. A textile or textile-like receiving surface is arranged to cooperate with the fastening tabs. The placing of the receiving surface is complementary to the placing of the fastening means. If the fastening means is arranged on the fastening tabs, then the receiving surface is arranged on the front part of the diaper or vice versa.

According to a further embodiment of the invention, where the fastening means is arranged on the fastening tabs of the diaper, the rear part of the diaper has also a textile or textile-like receiving surface, for fastening together of a folded-up, or rolled-up, diaper after use.

By arranging a layer with openings or pores on top of the self-adhesive, pressure sensitive layer, the need to use a special, removeable protective layer during transport and storage of a product provided with a fastening laminate is eliminated. A product provided with a laminate according to the invention can, during storage and transport, be folded together in a desired manner, without risk of sticking together.

It is further possible to completely determine the positioning of the fastening means on a product according to what is found to be suitable in order to achieve the required fastening characteristics, as no allowance has to be made for the risk of sticking together during packing and storage of the product.

The fastening means according to the invention permits certain and effective fastening onto a fastening surface made of textile or textile-like material. As the fastening means does not have parts intended to penetrate the receiving surface, the risk of damage to this surface in connection with use of the fastening means is avoided.

Furthermore, the fastening means has essentially equally good adhesion on different types of textile material, without the risk of traces of adhesive being left behind on the textile surface when the fastening means is removed. Further, it is possible to use a smaller amount of an adhesive with extremely high adhesive capability, as the covering layer of the fastening means reinforces the adhesive and prevents the occurrence of traces of adhesive being left behind.

Different areas of use can set different demands on the adhesive capability of the fastening means. For example, the fastening capability in a fastening means which is used to hold a sanitary napkin inside a pair of underpants is not as great as that for a fastening means which shall be used to hold together a diaper to a pants-like shape. Articles such as bibs, napkins, bed and seat protectors require comparatively low adhesive capability. With a fastening device according to the invention, it is possible to control the adhesive capability not only by changing the characteristics of the adhesive layer, but also by varying the characteristics of the covering layers. For example, the adhesive capability can be reduced by using a covering layer with relatively small openings, or through the use of a somewhat thicker covering layer. In a corresponding way, the adhesive capability can be increased with a looser or thinner covering layer.

In addition, the invention permits a simple and material-saving manufacture of a pressure sensitive, adhesive fastening means, as well as products equipped with fastening means according to the invention.

As a result of the fastening means, expensive and complicated folded tape tabs need to be used on a diaper according to the invention. The fastening tabs on a diaper according to the invention are easy to grip and fasten against the front part of the diaper. As the fastening tabs do not have to be loosened from a protective surface, they are easy to handle and can be made in a soft comfortable material which will not chafe or irritate the skin of the user.

BRIEF DESCRIPTION OF THE DRAWINGS

The invention shall be described more closely below with reference to the embodiments shown in the accompanying drawings.

DESCRIPTION

Figure 1:
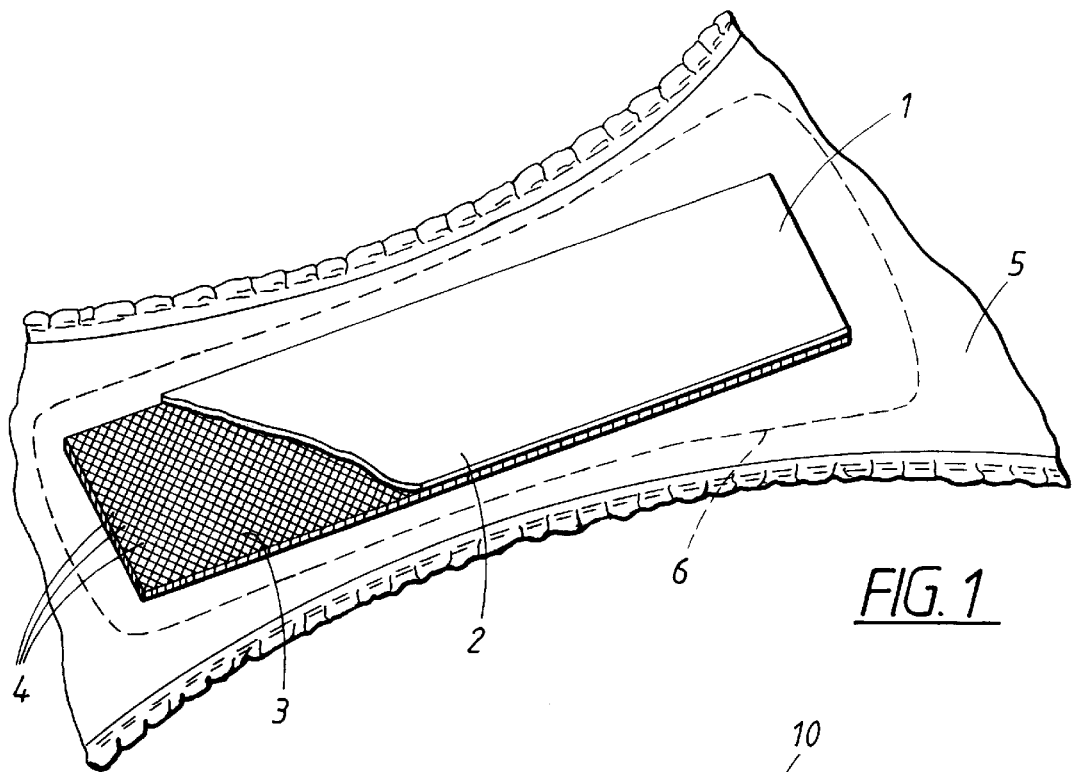
FIG. 1 shows in perspective view a fastening means according to the invention, attached to the crotch part on a pair of underpants.

The fastening means 1 shown in FIG. 1 is made of a laminate consisting of a layer 2 of self-adhesive, pressure sensitive adhesive, as well as, joined with the adhesive layer 2, a covering layer 3 made of an essentially inelastic, thin layer of material equipped with a plurality of small openings or pores 4. For the sake of clarity, the fastening means 1 has been shown with the adhesive layer 2 partially removed, so that the covering layer 3 is visible.

The fastening laminate 1 is applied in the crotch part of a pair of underpants 5, with the covering layer 3 facing towards the underpants. The contour of a sanitary napkin 6 is indicated around the fastening laminate.

The self-adhesive layer 2 is suitably made from a hot-melt adhesive material. Naturally, other types of adhesive materials with suitable characteristics can be used, for example water-based adhesives, curable adhesives, or adhesives with organic solvents. It is also possible to conceive of using a double-sided adhesive tape instead of a single adhesive layer.

The covering layer 3 can, for example, be a thin, fine-meshed plastic net, a perforated plastic film, a comparatively loose or perforated non-woven fibrous web, or a loose weave of natural or synthetic fibres. It is also possible to conceive that the covering layer consists of threads or fibres which are applied directly to the self-adhesive adhesive layer, without being joined together beforehand to form a coherent layer.

During use, the fastening means 1 is made to adhere to a textile or textile-like receiving surface 5 by being pressed against the receiving surface 5, with the covering layer 3 facing towards this surface. In this way, the adhesive layer 2 is brought into adhesive contact with the receiving surface 5 through the openings or pores 4 in the covering layer 3. The fastening means can only be fastened against a material which has a certain surface irregularity and formability, so that its surface can come into contact with the adhesive through the covering layer 3. The surface of the material should be porous, in other words have an irregular structure built up of fibres, particles, or similar with intermediate spaces or pores. Projecting elements on the receiving surface 5 can in this way penetrate into the pores or openings in the cover layer 3 of the fastening means 1 and further improve the contact between the adhesive layer 2 and the receiving surface 5. A "textile, or textile-like surface" is made, for example, by weaving, knitting, plaiting, crocheting or similar traditional manufacturing methods. The invention is also intended to include surfaces which are manufactured through more modern techniques, such as by different methods for the manufacture of fibrous webs known as non-woven materials, paper manufacturing processes, or similar. It is also conceivable that material with suitable surface characteristics can be made through casting or heat treatment of plastic material.

It is important that the openings or pores 4 in the covering layer 3 permit the adhesive to penetrate the covering layer 3 under the influence of pressure in a sufficiently high extent to bring about the desired joining between the fastening means 1 and the receiving surface 5. An important parameter is, in this connection, the available fastening area on the fastening means 1, in other words the part of the adhesive layer 2 on the fastening means 1 which is exposed through the openings or pores 4 in the covering layer 3. The fastening area needed for a particular fastening purpose is dependent on the adhesive capacity of the adhesive which is used, the size of the adhesive surface area and the desired adhesive force. These parameters are naturally different for different uses, and it is therefore impossible to give general values for the fastening area. For the acceptable adhesion of sanitary napkins on different types of panty material, it has, however, been found that a suitable fastening area should make up at least 30% of the surface of the fastening means.

Other significant parameters are the thickness of the covering layer 3 and the size of the openings or pores 4. For example, in general, an extremely thin material must have openings with a smaller dimension than that of a somewhat thicker material, in order to achieve the desired protective effect of the adhesive. In general, possible materials are thin loose non-woven materials with a surface weight of between 7–20 g/m². It is further possible to use non-woven material or net material with relatively coarse fibres or threads with a size in the order of 5–10 dtex. With coarser fibres or threads, the openings can be bigger, while finer fibres or threads in general require smaller openings. The distance between the openings in the covering layer should, however, not be more than approximately 3 mm and preferably not more than approximately 2 mm in order to achieve a sufficient adhesive capacity. An advantageous combination of high protective effect for the adhesive and a high adhesive capacity against textile or textile-like material is achieved generally with a thin, fine-meshed net or non-woven material with closely arranged openings or pores. The distance between two openings or pores in such a material amounts to only fractions of a millimeter and is of about the same size as the thickness of the fibres, or the threads in the material.

In order to facilitate the contact between the adhesive layer 2 and the receiving surface 5, the covering layer 3 should, however, be relatively thin. A proportionally thick covering layer 3, or extremely small openings or pores 4, obviously give a better protection for the adhesive layer 2 during storage and transport, but, at the same time, make it more difficult during use for the adhesive to penetrate the covering layer 3 so that a satisfactory adhesion is obtained. Preferably, the covering layer should not be more than approximately 0.5 mm thick and particularly preferred is a covering layer with a thickness which is less than 0.2 mm.

Further significant factors are the softness, elasticity and adhesive capacity of the adhesive layer 2. These characteristics naturally interplay with the characteristics of the covering layer 3, such as its thickness, the number of openings and the size of the openings or pores 4.

Consequently, a softer adhesive can more easily be made to penetrate a relatively thick covering layer, than a relatively hard adhesive. An adhesive with high adhesive ability does not require an equally large available connecting area as an adhesive with a lower adhesive capability.

Figure 2:
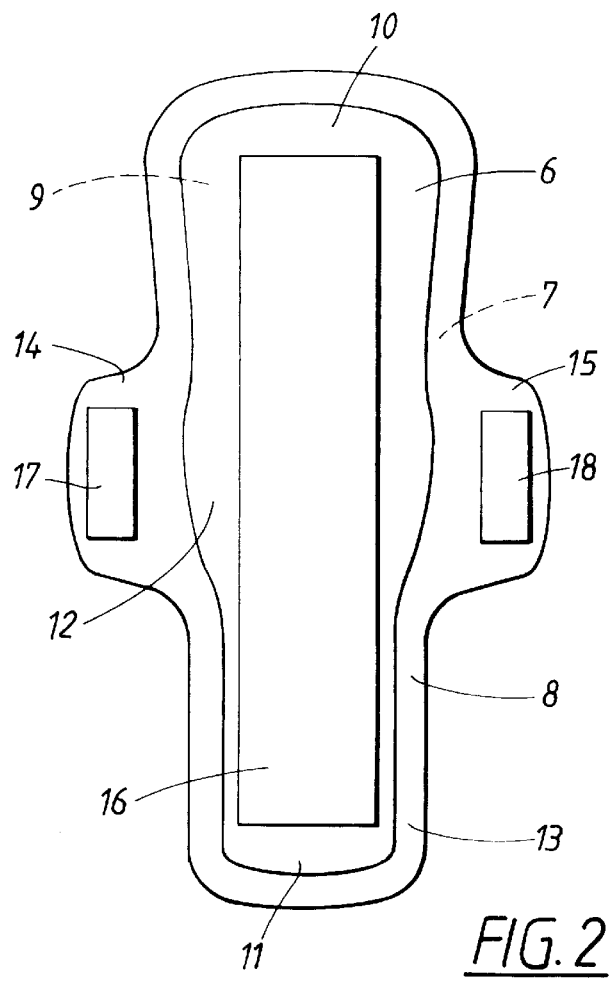
FIG. 2 shows a plan view of a sanitary napkin, seen from the side facing away from the user during use.

The sanitary napkin 6 shown in FIG. 2 comprises a first liquid-permeable casing layer 7 arranged on the side of the sanitary napkin 6 which during use is intended to face towards the user, a second, liquid-impermeable casing layer 8, arranged on the side of the sanitary napkin which during use is intended to face away from the user, and an absorption body 9 enclosed between the two casing layers 7, 8. The sanitary napkin 6 has further a front part 10, intended during use to face towards the front of the user, a rear part 11, intended during use to face towards the rear of the user, and a crotch part 12 arranged between the front part 10 and the rear part 11. The sanitary napkin 6 has an essentially elongated trapezoidal form, wherein its front part 10 is somewhat wider than the rear part 11.

Both casing layers 7, 8 extend out around the periphery of the sanitary napkin 6 and are mutually connected in the extended casing parts 13. On both sides of the absorption body 9, at the crotch part 12 of the sanitary napkin 6, the projecting casing parts 13 form fastening tabs, or wings 14, 15. These are shaped so that during use they can be bent around the leg edges of a pair of underpants and be fastened against the outside of the underpants, whereby the underpants are protected from leakage of body fluids.

The sanitary napkin 6 further comprises three fastening means according to the invention, one of which forms a longitudinal fastening region 16 on the liquid-impermeable casing layer 8 of the sanitary napkin 6. Two further fastening means are arranged on the wings 14, 15, on the sanitary napkin 6, in the form of small fastening regions 17, 18, on the liquid-impermeable casing layer 8. Each of the fastening means comprises a pressure sensitive adhesive layer 2 which is arranged on the liquid-impermeable layer 8, and a covering layer 3 arranged outside the adhesive layer 2, in the form of a proportionally loose woven plastic net. The elongated fastening region 16 serves during use to hold the sanitary napkin 6 inside a pair of underpants, while the fastening regions 17, 18 on the wings 14, 15, are intended during use to be fastened against the underside of the crotch part of the underpants. The covering layer 3 of the fastening means protects the adhesive layer 2 during transport and storage of the sanitary napkin 6, but, during use, allows good fastening of the sanitary napkin 6 inside the user's underpants.

Figure 3:
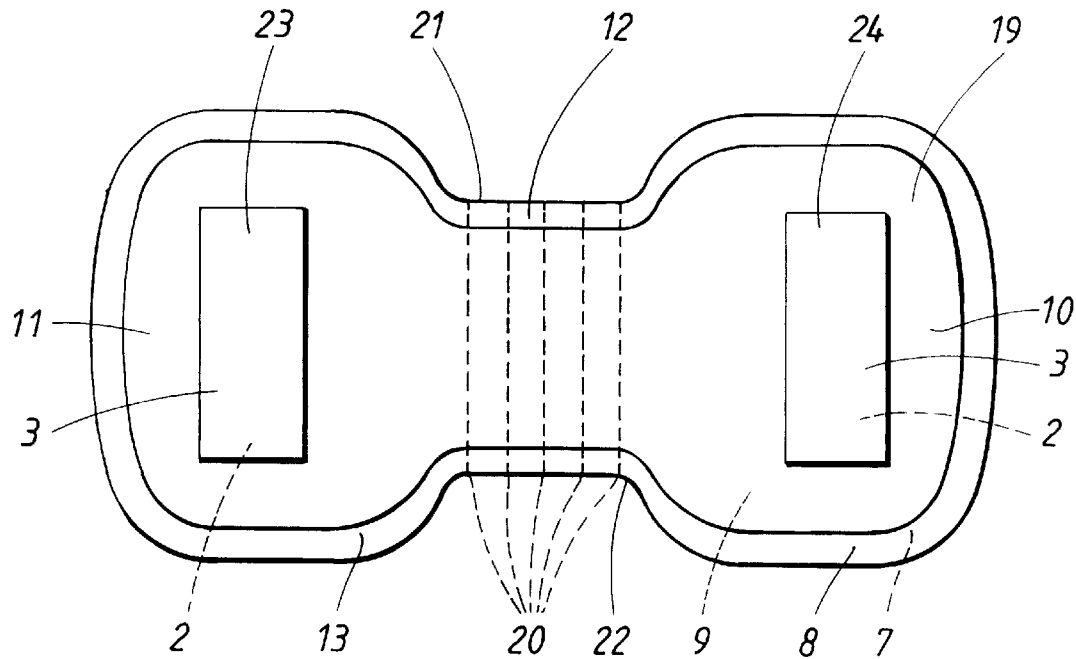
FIG. 3 shows a plan view of an incontinence pad, seen from the side facing away from the user during use.

The incontinence pad 19 shown in FIG. 3 has primarily the same construction as the sanitary napkin 6 in FIG. 2. Corresponding structural elements have therefore been indicated with the same reference numerals as in FIG. 2.

The incontinence pad 19 has a first, liquid-permeable casing layer 7, a second, liquid-impermeable casing layer 8, and an absorption body 9 enclosed between the casing layers 7, 8. When the incontinence pad is to be used, it is placed inside the underpants of a user, with the liquid-permeable casing layer 7 facing towards the user and the liquid-impermeable casing layer 8 facing towards the underpants.

Furthermore, the incontinence pad is essentially hour-glass shaped, with a front part 10, a rear part 11, and a narrower crotch part 12 arranged between the front and rear parts 10, 11. Transverse elastic means 20 in the form of threads, tapes or similar, are arranged in the crotch part 12, between the two longitudinal side edges 21, 22 of the incontinence pad. The elastic means are arranged in the incontinence pad 19 of FIG. 3, between the liquid-permeable casing layer 7 and the absorption body 9, but it is naturally also possible to arrange the elastic means inside the absorption body 9 or on the liquid-impermeable casing layer 8.

Two fastening means, in accordance with the invention, are arranged on the liquid-impermeable casing layer 8 of the incontinence pad 19, one on the front part 10 of the incontinence pad and one on its rear part 11, forming a front and a rear fastening region 23, 24 for fastening the incontinence pad inside the pants of the user.

Figure 4:
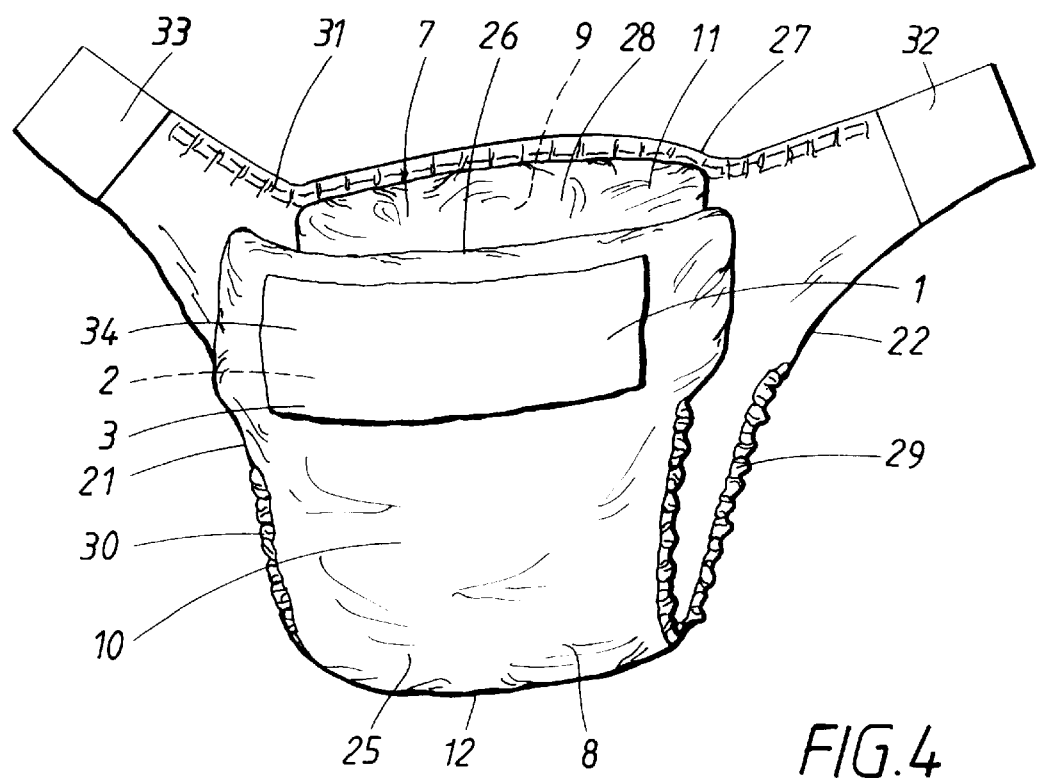
FIG. 4 shows a front view of a diaper.

The diaper 25 shown in FIG. 4 has also the same principal construction as the absorbent products shown in FIGS. 2 and 3 and consequently the same reference numbers have been used for corresponding structural elements.

The diaper 25 comprises a first, liquid-permeable casing layer 7, intended during use to face towards the user, a second, liquid-impermeable casing layer 8, intended during use to face away from the user, and an absorption body 9 enclosed between the two casing layers. The diaper 25 is shaped so that during use it surrounds the lower part of the trunk of the user in a way similar to a pair of pants. For this purpose, the diaper has a front part 10, intended during use to face towards the front of the user and to be lying over the stomach of the user, a rear part 11 intended during use to face towards the rear part of the user and to be lying over the seat of the user, and a narrower crotch part 12, arranged between the front and rear parts 10, 11, intended during use to be arranged in the crotch area, between the legs of the user. Furthermore, the diaper 25 has a front waist edge 26, as well as a rear waist edge 27, which together form the waist opening 28 of the diaper.

The diaper 25 further comprises elastic means 29, 30, which are arranged along the longitudinal side edges 21, 22 of the diaper 25 and which form elastic leg edges when the diaper is used, as well as elastic means 31, which are arranged along the rear waist edge 27 of the diaper.

Fastening tabs 32, 33 are arranged at the longitudinal side edges 21, 22 on the rear part 11 of the diaper near the rear waist edge 27. The fastening tabs are made of a soft, flexible textile or textile-like material, appropriately non-woven web, known as non-woven, and are intended to co-operate with the fastening means 1 arranged on the front part 10 of the diaper, in accordance with the invention. The fastening means 1 is made of a pressure sensitive adhesive layer 2 applied to the front part 10 of the diaper, as well as a covering layer 3 arranged on top of the adhesive layer, made of loose non-woven material, through which the adhesive layer 2 is accessible for fastening of the fastening tabs 32, 33. As the fastening means 1 forms a longitudinally extending fastening region 34 along a large part of the front waist edge 26 of the diaper, it is possible to adjust the size of the waist opening 28 according to the body of the user, in order to achieve the best possible fit.

The covering layer 3 can be of essentially the same size and shape as the adhesive layer 2, or can extend over a larger part of the liquid-impermeable layer 8. In the latter case, it can be necessary to, for example with colouring, show the extent of the fastening region 34.

It is further possible to instead arrange fastening means on the fastening tabs, whereby these co-operate with a textile, or textile-like receiving surface on the front part of the diaper. In this embodiment, the receiving surface can be made arbitrarily large and can, for example, extend over the whole of the liquid-impermeable casing layer of the diaper, whereby the fastening tabs can be fastened anywhere on the outside of the diaper. In this way, the possibility of individually adjusting the diaper to the body of the user is increased. Furthermore, after use, the diaper can be rolled or folded together to form a package, wherein the fastening tabs serve as closing means for the package.

The invention is not limited to the embodiments described here. For example, the fastening means can extend over the whole of the surface of the liquid-impermeable layer of a sanitary napkin or an incontinence pad. In this way, manufacturing of the product is simplified and, at the same time, the liquid-impermeable layer is granted an attractive, textile-like surface.

It is further possible to use a fastening means according to the invention to fasten bed protectors or seat covers against textile surfaces, or to fasten absorbent inserts inside special diaper holders or diaper pants.

A series of further areas of applicability are conceivable within the scope of the patent claims.

What is claimed is:

1. A fastening device for removeable fastening on textile or textile-like material surfaces, comprising a self-adhesive, pressure sensitive adhesive layer with a first surface intended to be permanently joined to a substrate and a second surface intended to serve as a fastening surface onto the textile or textile-like material surface, wherein a non-adhesive covering layer having a thickness which does not exceed 0.5 mm and having a plurality of penetrating openings or pores arranged essentially perpendicularly to the plane of the covering layer is arranged on and affixed to the fastening surface of the adhesive layer and wherein the distance between two adjacent openings or pores in the covering layer does not exceed 3 mm, wherein the covering layer comprises an essentially incompressible nonwoven material or net material being made of relatively coarse threads or fibres in the order of 5–10 dtex and having a surface weight between 7 g/m$^2$ and 20 g/m$^2$, wherein the relation between the dimension of the openings or pores in the covering layer and the coarseness of the fibers is such that the fastening device exhibits adhesion onto textile or textile-like material surfaces, but essentially no adhesion onto smooth material surfaces.

2. Fastening device according to claim 1, wherein the non-adhesive covering layer is made of a plastic net.

3. Fastening device according to claim 1, wherein the non-adhesive covering layer is made of a layer of nonwoven fibrous web, or a loose weave.

4. Fastening device according to claim 1, wherein the distance between two adjacent openings or pores in the covering layer does not exceed 2 mm.

5. An absorbent product, such as a sanitary napkin, a light incontinence pad, or similar product, comprising an absorption body enclosed in a casing, as well as a fastening means arranged on the outside of the casing comprising a pressure-sensitive adhesive layer for fastening of the product onto a textile or textile-like receiving surface and a covering layer comprising an essentially incompressible, non-adhesive nonwoven material or net material having a thickness which does not exceed 0.5 mm and which has a plurality of penetrating openings or pores therethrough, is arranged on and fastened to the surface of the adhesive layer which is facing away from the product, wherein the distance between two adjacent openings or pores in the covering layer does not exceed 3 mm, and wherein the covering layer is made of relatively coarse threads or fibers in the order of 5–10 dtex and has a surface weight between 7 g/m$^2$ and 20 g/m$^2$ and wherein the relation between the dimension of the openings or pores in the covering layer and the fiber coarseness is such that the fastening device exhibits adhesion onto textile or textile-like material surfaces, but essentially no adhesion onto smooth material surfaces.

6. A diaper, comprising a first liquid-impermeable casing layer, a second liquid-impermeable casing layer, wherein both casing layers are mutually joined around an absorption body enclosed between the casing layers, and further comprising a front part, a rear part, and a narrower crotch part arranged between these two parts, and further having two longitudinal side edges and a front waist edge and a rear waist edge, whereby both waist edges are shaped so as to together surround the waist of the user and thereby form a waist opening of the diaper, and further comprising fastening tabs which are arranged at the longitudinal side edges near the rear waist edge and are intended to be fastened against the front part for fastening together of the diaper to a pants-like shape, wherein each fastening tab comprises a fastening means comprising a pressure sensitive adhesive layer arranged on the tab, and wherein a non-adhesive covering layer having a thickness which does not exceed 0.5 mm, and having a plurality of penetrating openings or pores therethrough, is arranged on and fastened to the surface of the adhesive layer facing away from the tab, wherein the distance between two adjacent openings or pores in the covering layer does not exceed 3 mm, the covering layer comprises an essentially incompressible nonwoven material or net material, and wherein the covering layer is made of relatively coarse threads or fibers in the order of 5–10 dtex and has a surface weight between 7 g/m$^2$ and 20 g/m$^2$ and wherein the relation between the dimension of the openings or pores in the covering layer and the fiber coarseness is such that the fastening device exhibits adhesion onto at least one receiving surface with textile, or with textile-like characteristics, the receiving surface being arranged on the front part of the diaper.

7. Diaper according to claim 6, wherein the liquid-impermeable casing layer on the rear part of of the diaper has a textile or textile-like receiving surface, for fastening together of a folded-up, or rolled-up, diaper after use.

8. A diaper, comprising a first liquid-permeable casing layer, a second liquid-impermeable casing layer, said both casing layers being mutually joined around an absorption body enclosed between the casing layers, and further comprising a front part, a rear part, and a narrower crotch part arranged between these two parts, and further having two longitudinal side edges, a front waist edge and a rear waist edge, which two waist edges are shaped so as to together surround the waist of a user and thereby form a waist opening of the diaper, and further comprising fastening tabs which are arranged at the longitudinal sides, near the rear waist edge and are intended to be fastened against the front part for fastening together of the diaper to a pants-like shape, wherein at least one receiving surface on the front part of the diaper has a fastening means comprising a pressure sensitive adhesive layer arranged on the liquid-impermeable casing layer of the diaper, and that an essentially incompressible, non-adhesive covering layer being made of relatively coarse threads or fibers in the order of 5–10 dtex and having a surface weight between 7 g/m$^2$ and 20 g/m$^2$, and a plurality of penetrating openings or pores therethrough, is arranged on top of and fastened to the surface of the adhesive layer facing away from the liquid-impermeable casing layer, wherein the covering layer has a thickness which does not exceed 0.5 mm and wherein the distance between two adjacent openings or pores in the covering layer does not exceed 3 mm and wherein the relation between the dimension of the openings or pores in the covering layer and the fiber coarseness is such that the fastening device exhibits adhesion onto textile or textile-like material surfaces, but essentially no adhesion onto smooth material surfaces and that each fastening tab has a surface with textile, or textile-like characteristics, which is intended to co-operate with the fastening means on the front part of the diaper.

* * * * *